United States Patent [19]

Barrett

[11] Patent Number: 4,628,931

[45] Date of Patent: Dec. 16, 1986

[54] MEDICAL TREATMENT METHOD

[76] Inventor: Harold F. Barrett, Rte. 1, Box 262A, London, Ark. 72847

[21] Appl. No.: 611,974

[22] Filed: May 18, 1984

Related U.S. Application Data

[63] Continuation-in-part of Ser. No. 354,361, Mar. 3, 1982, Pat. No. 4,469,103.

[51] Int. Cl.$^4$ .............................................. A61F 7/00
[52] U.S. Cl. ...................................................... 128/399
[58] Field of Search ................................ 128/399–402, 128/362

[56] References Cited

U.S. PATENT DOCUMENTS

| | | | |
|---|---|---|---|
| 1,327,207 | 4/1920 | Lidberg . | |
| 1,572,300 | 5/1926 | Max . | |
| 1,995,302 | 3/1935 | Goldstein | 128/254 |
| 2,058,780 | 8/1936 | Elliott | 128/401 |
| 2,190,384 | 11/1940 | Newman | 128/400 |
| 2,346,245 | 7/1944 | Zichlin | 128/401 |
| 2,466,042 | 4/1949 | Reich et al. | 128/401 |
| 2,734,508 | 1/1956 | Kozinski | 128/401 |
| 3,089,033 | 5/1963 | Fujisawa | 128/322 X |
| 3,496,942 | 3/1970 | Shipley | 128/401 |
| 3,848,607 | 7/1974 | St. Clair | 128/400 |
| 4,121,592 | 6/1978 | Whalley | 128/413 |
| 4,160,455 | 8/1979 | Law | 128/400 |
| 4,181,132 | 1/1980 | Parks | 128/399 |
| 4,190,053 | 4/1980 | Sterzer | 128/399 |
| 4,398,535 | 8/1983 | Guibert | 128/399 |
| 4,461,299 | 7/1984 | Guibert | 128/399 |
| 4,501,275 | 2/1985 | Maahs | 128/399 X |

FOREIGN PATENT DOCUMENTS 2731744  2/1979  Fed. Rep. of Germany ...... 128/804

OTHER PUBLICATIONS

Warren, "Preliminary Study . . . Tumor Cases", American Journal of Roent. & Radium Therapy, vol. XXXIII, No. 1, Jan., 1935, pp. 75–87.
Law et al, "New Apparatus . . . Neoplasma", IEEE Trans. Biomedical Engineering, vol. BME-26, No. 3, Mar. 1979, pp. 175–177.
Yerushalmi, "Treatment of a Solid Tumor . . .", Europ. J. Cancer, vol. 12, pp. 807–813, 1976.
Yerushalmi, "Combined Treatment of a Solid Tumor . . .", Br. J. Cancer, 1978, 37, 827–832.

*Primary Examiner*—Lee S. Cohen
*Attorney, Agent, or Firm*—Kerkam, Stowell, Kondracki & Clarke

[57] ABSTRACT

Conditions in a living body produced by injury or defective cells, such as musculo-skeletal conditions and the like, are treated by applying to the body infrared electromagnetic energy having a wavelength such that the energy is absorbed by the cells and having an amplitude that is effective to treat the condition, the energy being derived from a flow of heated air directed to an adjacent external area of the body, the wavelength being determined by the temperature of the air and the amplitude being determined by the flow rate.

24 Claims, 4 Drawing Figures

MEDICAL TREATMENT METHOD

This application is a Continuation-in-Part of prior application Ser. No. 354,361, filed Mar. 3, 1982, now U.S. Pat. No. 4,469,103, issued Sept. 4, 1984, the disclosure of which is incorporated by reference herein.

BACKGROUND OF THE INVENTION

This invention relates generally to medical treatment methods and apparatus, and more particularly to methods and apparatus for treating conditions in a living body produced by defective cells or by injury, such as musculo-skeletal conditions and the like.

The above-identified application discloses the use of infrared electromagnetic energy for the treatment of conditions in a living body produced by defective cells, and specifically illustrates the invention in the context of treating tumors. As disclosed therein, the infrared electromagnetic energy is derived from a flowing fluid and is applied directly to the affected area by means of surgically implanted tubes which carry the fluid. The energy is selected to have a wavelength such that it is absorbed by the cells and a cellular-type resonance is produced, and the amplitude of the energy is adjusted so as to cause substantial destruction of defective cells without destroying healthy cells.

There are, however, a number of conditions other than tumors in the living body produced both by defective cells or by injury for which conventional medical, surgical or chiropractic treatment methods are either totally or partially ineffective, or otherwise disadvantageous. Among these are various musculo-skeletal conditions such as edema of a joint, ligament, tendon, muscle or nerve, or related tissues, conditions such as neuralgias and arachnoiditis produced by scar tissue, and conditions produced by calcium or other deposits in joints, tendons or ligaments, to mention a few. The present disclosure extends the techniques of the prior application to the treatment of these and other conditions produced by defective cells or injury.

SUMMARY OF THE INVENTION

The present invention provides new and improved methods and apparatus for treating conditions such as musculo-skeletal conditions and the like in living bodies by enabling the selective destruction of defective cells with little or no damage to healthy cells and few if any adverse side effects. Advantageously, treatment methods in accordance with the invention are non-invasive, requiring no surgical implantation of tubes, thereby avoiding the necessity for sterilization of the apparatus and the possibilities of infection. Treatment methods in accordance with the invention have been shown to be remarkably effective in very short periods of time for treating various conditions such as musculo-skeletal conditions and the like, and may be practiced with simple apparatus.

Briefly stated, in accordance with the invention, conditions in a living body that are produced by injury or by defective cells are treated by applying infrared electromagnetic energy of selected wavelengths to an affected area of the body, and adjusting the amplitude of the energy to a value that is effective to treat the condition. For conditions produced by defective cells, the energy amplitude is effective to cause substantial destruction of defective cells without substantially destroying healthy cells. The electromagnetic energy is applied externally to the body by a gaseous carrier fluid having a temperature so as to produce a temperature at the location of the condition that is within the normal operating temperature range of the body, and the amplitude of the energy is adjusted to the effective value by adjusting the flow rate of the fluid that is applied at such location.

More particularly, the infrared electromagnetic energy has a distribution of wavelengths related to the absolute temperature of the flowing fluid, and the temperature is selected so as to provide a dominant wavelength, in the 9–10 micron range, for example, that is matched to the cell sizes of the living body so that the cells absorb the energy efficiently. The amplitude of the energy is related to the flow rate of the fluid, and, in general, is porportional thereto.

DESCRIPTION OF THE PREFERRED EMBODIMENT

In said prior application, it was disclosed that conditions in a living body produced by defective or abnormal cells could be treated effectively and with remarkable results by applying to the defective cells infrared electromagnetic energy having a wavelength selected such that the energy is absorbed by the cells and a cellular-type resonance is produced, and having an amplitude so as to substantially destroy defective cells without substantially destroying healthy cells. It was theorized therein that under normal conditions, the cells within a living body absorb infrared electromagnetic energy derived from the blood flowing through the blood vessels. The infrared electromagnetic energy passes through the blood vessel walls to the cells, and is believed to supply the major energy requirements of the cells. The wavelength of the energy is related (by Wien's Law) to the absolute temperature of the blood, and has a dominant wavelength determined by the average blood temperature and a wavelength distribution about the dominant wavelength due to blood temperature variations. The amplitude of the energy supplied to the cells is porportional to the blood flow rate. The normal operating temperature range of the human body may be considered to be approximately 96° F. to 104° F. which corresponds to an infrared electromagnetic energy wavelength of approximately 9.25 to 9.38 microns. The energy passes through the blood vessel walls and is absorbed by the cells. It causes the cells to expand and resonate at a frequency dependent upon the cell dimensions, thus providing a work potential. Good or healthy cells have thin outer walls, are highly elastic, and are tightly bound to other good cells. As a result, the energy is distributed or amortized over large numbers of cells, and externally applied energy may actually be used to beneficially energize healthy cells. If the energy supplied to the cells becomes too great, the cells may be unable to absorb the energy and may be destroyed by breaking of the cell wall and/or the nucleus.

Defective cells include alien cells taken into the body, e.g., viruses, as well as cells produced by the body, and are generally being destroyed rapidly by the ambient energy within the body. Defective cells produced by the body are generally about the same size as the good cells of the specific organ or tissue that produces them. Thus, they absorb energy at about the same wavelengths as good cells and resonate at about the same frequencies. However, defective cells generally have thicker walls than do good cells, are not as elastic, and are more loosely bound to each other than are good cells. As a result, defective cells are unable to withstand as high an energy level as good cells, and, in fact, are capable of being destroyed at energy levels which beneficially energize healthy cells. Thus, conditions within a living body that are produced by defective cells may be effectively treated by applying to an affected area of the body external infrared electromagnetic energy having a wavelength such that it is absorbed by the cells within the affected area and having an energy amplitude high enough to cause selective destruction of defective cells without causing damage to healthy cells. The defective cells, which do not have the same elasticity or tight inter-cell bonds as good cells, are unable to absorb all of the externally applied energy and are destroyed.

In the prior application, these principles were applied to the treatment of cancerous tumors with remarkably effective results. There, the energy was derived from a flowing fluid and was applied to the tumor either by passing water or other fluid of an appropriate temperature and flow rate through a surgically implanted tube adjacent to the tumor, or by passing air of the appropriate temperature and flow rate over the tumor, and then withdrawing the air from the body, also using surgically implanted tubes adjacent to the tumor.

Although significant results are achieved, the previously described treatment methods and apparatus have the disadvantage of being invasive techniques. As will be described shortly, a simpler, non-invasive technique has been found for applying external infrared electromagnetic energy to an affected area body. In addition to treating tumors, the technique has been found to be particularly effective for treating various other conditions produced by defective cells in a living body or by injury. Musculo-skeletal conditions which have been found to be particularly susceptible to treatment include chronic arthritis or bursitis of joints, tendonitis, epicondylitis, rheumatoid arthritis, fibromyositis, contractures, myositis, edema of intravertebral discs or associated tissues, neuralgias and arachnoiditis or similar conditions due to post-surgical scar tissue formation, acute sprains, and conditions due to the formation of calcium deposits in joints. The invention has also been found to be remarkably effective in dissolving scar tissue, in energizing healthy cells to promote healing and to provide organ stimulation or skin rejuvenation, in forcing excess liquid from cells to prevent or reduce swelling due to inflammation or injury, in affording rapid blood coagulation to control bleeding of open cuts or wounds, and in treating various respiratory conditions such as colds or flu. These and other conditions have been treated very successfully utilizing the principals of the invention, as will be described hereinafter. First, however, improved apparatus and methods for treating such conditions will be described. Then, examples of actual treatments will be presented.

Figure 1:
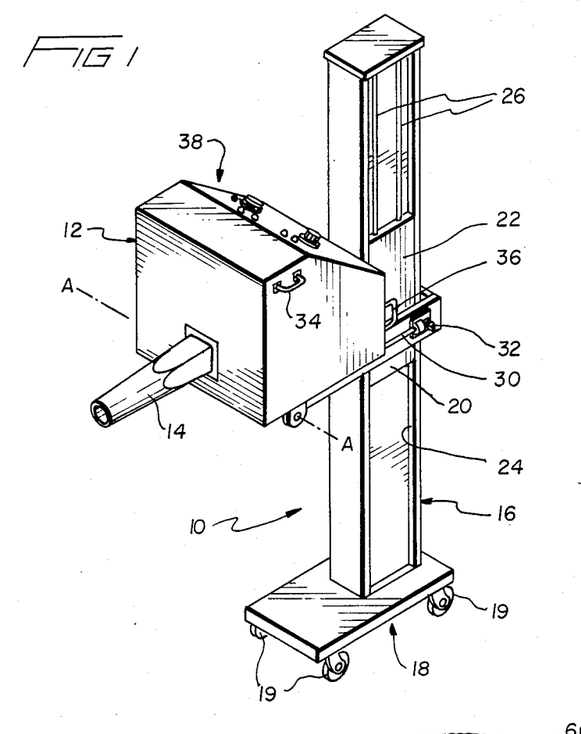
FIG. 1 is a perspective view illustrating treatment apparatus in accordance with the invention.

FIG. 1 illustrates the external appearance of a preferred form of a treatment apparatus 10 in accordance with the invention. As shown, the apparatus may comprise a treatment unit 12 for supplying infrared electromagnetic energy via a nozzle 14, as will be described shortly. The treatment unit may be carried on an upright portion 16 of a moveable stand or cart 18 having rollers 19 so that the stand may be easily moved, and formed to enable the treatment unit to be raised and lowered easily. The treatment unit may be supported on the upright portion by a pair of horizontal members 20 connected to corresponding slideable plates 22 disposed within vertical channels 24 on opposite sides of upright portion 16 (only one horizontal member 20, slideable plate 22 and vertical channel 24 being illustrated in the figure). The slideable plates 22 may be connected, as by cables 26, to counterweights (not illustrated) disposed within the interior of upright portion 16 of the stand, or to some other well-known mechanism, e.g., a hand crank, so as to enable the vertical position of the treatment unit to be varied easily. The treatment unit may be pivotally connected to the horizontal members 20 so as to enable the treatment unit to be rotated (counterclockwise in the figure from the horizontal positon shown) about a horizontal axis A—A. Preferably, the treatment unit is rotatable through an angle of 90°, and the stand may include a latch arrangement (which may be of conventional design) controlled by a rod 30 connected to an operating handle 32 so as to enable the treatment unit to be latched at a desired rotational position. Handles 34 and 36 may be located on the treatment unit to facilitate its positioning. The foregoing arrangement conveniently enables the treatment unit to be moved about and readily positioned to permit treatment of an affected area of the body.

Figure 2:
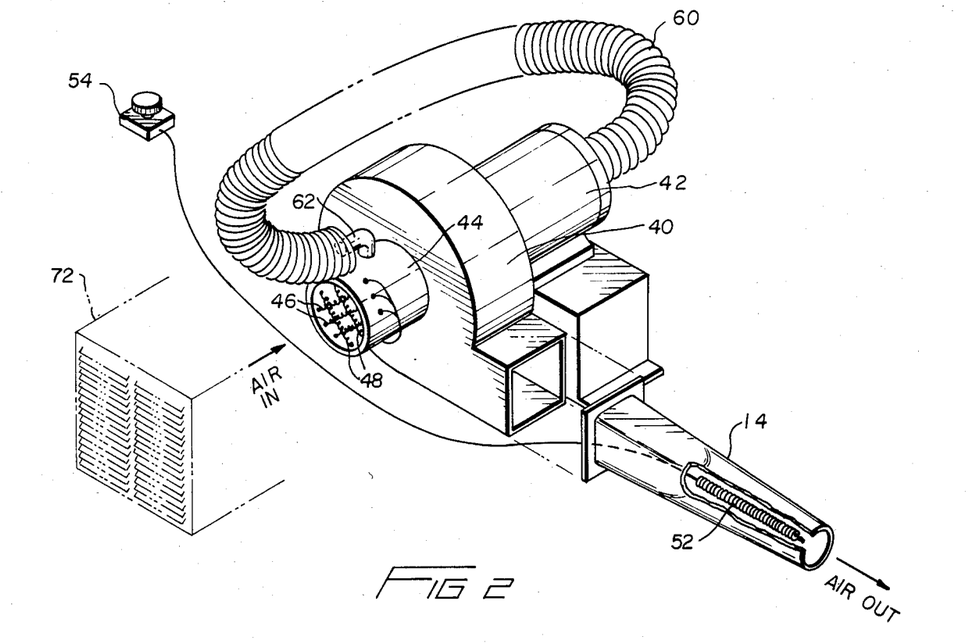
FIG. 2 is a perspective view partially broken away illustrating a portion of the apparatus of FIG. 1.

Treatment unit 12 is designed to apply infrared electromagnetic energy to a localized external area of the body adjacent to an area containing defective cells. The energy is applied via nozzle 14 by a heated gaseous carrier fluid, e.g., air, having a temperature so as to produce a desired internal body temperature at the affected area that is within the normal operating temperature range of the body. The amplitude of the energy applied is adjusted by adjusting the flow rate of the gaseous fluid to a value that is effective to substantially destroy defective cells without substantially destroying healthy cells. Operating controls and indicators for the treatment unit may be included on a front panel 38 thereof. FIG. 2, which shows some of the internal components of the treatment unit, illustrates a preferred arrangement for deriving a heated air flow, and FIG. 3 is an electrical schematic diagram of the treatment unit.

As shown in FIG. 2, the treatment unit may include a blower 40 and an associated drive motor 42 arranged to produce an air flow through nozzle 14. The blower, which preferably has a capacity of the order of 540 cubic feet per minute (CFM) may be a Dayton Model 2C820 blower, and the blower motor may be a Dayton Model 5K586 motor. Inlet air to the blower passes through a cylindrical member 44 in which is disposed a pair of heating coils 46 and 48 which heat the inlet air. Heating coil 46 may be a 9.9 ohm/1300 watt coil, and heating coil 48 may be an 8.8 ohm/1400 watt coil. As shown in FIG. 3, a switch 50, which may be disposed on the front panel of the treatment unit, enables either of the heating coils to be selected. Heating coil 46 may be employed when the ambient temperature in the treatment room is normal, and heating coil 48, which produces somewhat greater heat, may be employed when the ambient temperature is cool. The heating coils may be controlled by an adjustable thermostat (such as a Robert Z91712-00-24) comprising an elongated element 52 disposed within nozzle 14 and connected to a variable temperature controller 54 which may be disposed on the front panel of the treatment unit. The thermostat measures the temperature of the air flowing through nozzle 14 and, as indicated in FIG. 3, cycles AC power to the selected heating coil so as to maintain a desired air temperature. An indicator, such as a pilot light 56 connected as indicated in FIG. 3, may be disposed on the front panel to indicate the cycling of the heater coil.

Heat from blower motor 42 may also be used to assist in heating the inlet air to the blower. As shown in FIG. 2, a heat duct 60, as of flexible ducting material, may have one end connected to the blower motor and another end disposed about the inlet opening of a smaller diameter right-angled tubular member 62 connected to cylindrical member 44. This creates a venturi effect that pulls heat from the motor into the inlet of the blower, thereby enabling heat which would otherwise be wasted to be usefully employed.

Figures 3, 4:
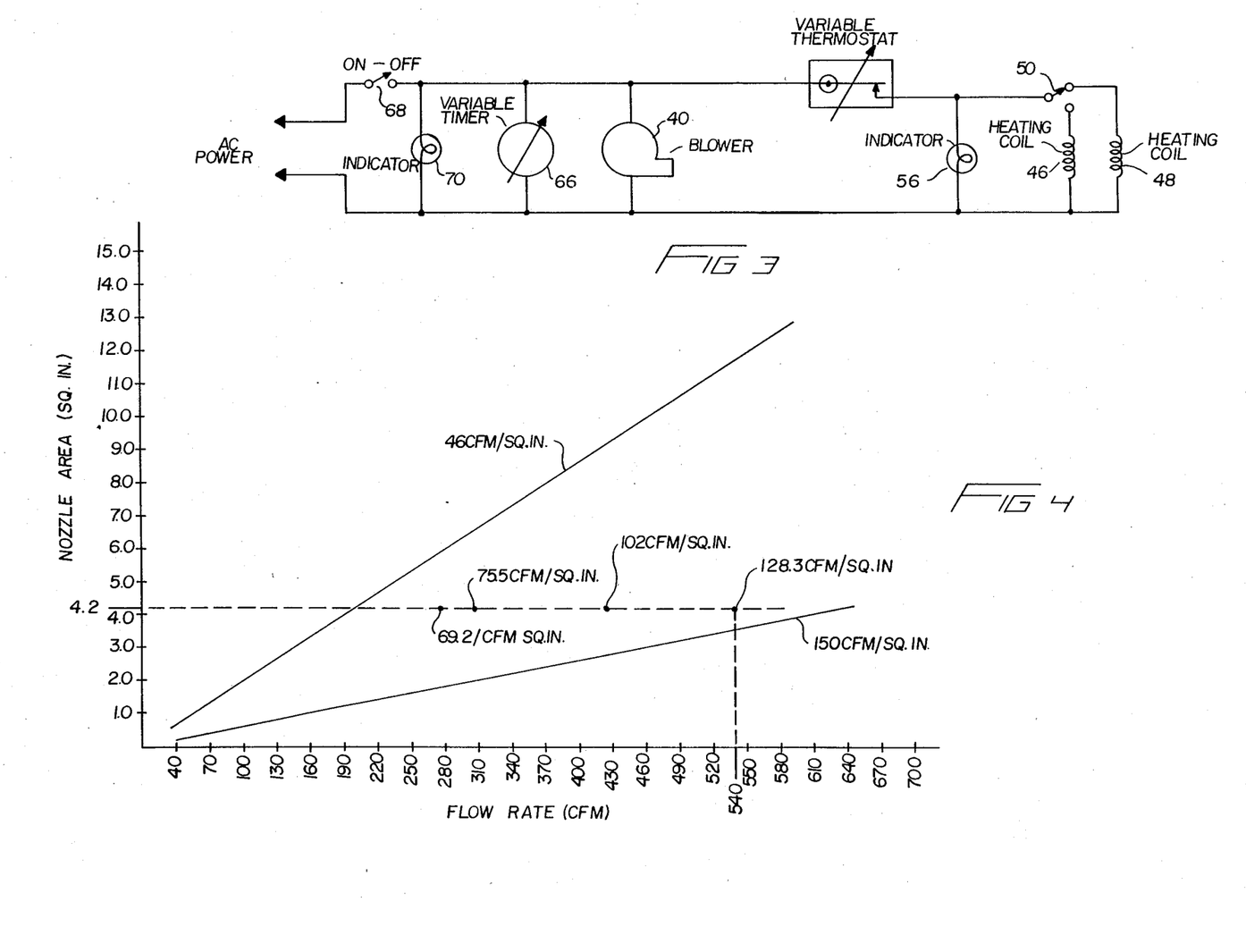
FIG. 3 is an electrical schematic diagram of the apparatus.
FIG. 4 is a graph illustrating a preferred operating range for the apparatus of FIG. 1.

As further shown in FIG. 3, the treatment unit may also include a variable electrical timer 66 disposed on the front panel and arranged to control an indicator (not shown), such as an alarm, for timing the length of a treatment. An ON-OFF switch 68 for controlling power to the unit and an indicator light 70 may also be included on the front panel of the unit. To enable the air flow produced by the treatment unit to be varied, an adjustable air baffle 72 (shown in phantom lines) may be disposed at the inlet of cylindrical member 44, or, alternatively, a variable speed blower motor may be employed.

In operation, a desired outlet air temperature and flow rate is set, and the treatment unit is positioned such that the outlet air from the nozzle is directed perpendicular onto the bare skin at an external area of the body adjacent to an internal area which is to be treated and such that the outlet of the nozzle is a predetermined distance from the body. The energy penetrates to the internal area through the skin pores and by resonating the cells in the skin. The operating parameters of the treatment unit, which include air temperature and flow rate, distance between the body and the outlet of the nozzle, and the treatment time, may be selected in accordance with the type of condition treated. Preferred operating parameters and ranges are as follows.

The wavelength of the energy applied to the affected area is determined by the outlet air temperature from the nozzle, and the energy amplitude is determined by the flow rate. It is desired that the temperature at the point of treatment be in the normal range of 96°104° F. with a median temperature of the order of 102°-104° F. for treating most conditions. Since bone cells tend to be somewhat smaller than tissue cells, conditions such as arthritis tend to respond better to temperatures in the upper portion of the range and a median temperature of 104° F. is preferred for treating bone conditions. To provide a desired temperature at the point of treatment, the outlet air temperature is measured at the nozzle outlet, as with a digital thermometer (not illustrated), until the temperature stabilizes at the desired value. The temperature is adjusted to be somewhat higher than the desired internal temperature to accommodate for temperature losses between the outlet of the nozzle and the point of treatment. In humans, there is approximately a 2.6° F. differential between skin and internal body temperature. Also, there is a 1°-2° F. temperature loss between the outlet of the nozzle and the skin for typical treatment distances of the order of 3-8 inches. Accordingly, the thermostat may be set to provide an outlet air temperature of the order of 3°-5° F. greater than that desired at the point of treatment. The thermostat is preferably adjustable over a range of about 98°-108° F. and is preferably capable of holding the outlet air temperature to within about ±1°-1.5° F. During a treatment, the outlet air temperature may be checked periodically to ensure it remains at the desired setting. Significantly, the treatment temperatures employed by the invention are within the normal operating temperature range of the body, in contrast to known hyperthermic treatment methods such as diathermy and similar methods.

For a given size nozzle opening, energy amplitude varies with flow rate and in general is porportional thereto. Preferably, the flow rate and/or nozzle size is selected so as to provide a flow rate per unit area in the range of 46 CFM/sq.in. to 150 CFM/sq.in. This operating range is illustrated in the graph of FIG. 4 as the area between the two lines labeled 46 CFM/sq.in. and, 150 CFM/sq.in. For a nozzle diameter of 2.315 inches (area approximately 4.2 sq.in.) and a 540 CFM blower, a flow rate per unit area of the order of 128.3 CFM/sq.in. may be obtained, as indicated. By holding the nozzle diameter constant and controlling the flow rate, the operating point will move along the horizontal dotted line. Several different operating points at which the invention has been operated are shown in the figure. In general, it has been found that the results obtained improve as the flow rate per unit area increases. Below approximately 46 CFM/sq.in., energy amplitude is too low to be effective and in some instances may actually promote the growth of defective cells, as in tumors, for example. Above approximately 150 CFM/sq.in., experiments on mice and chickens have shown some evidence of good cell damage, and above this value there exists the possibility of good cell damage in humans. Energy amplitudes corresponding to flow rates per unit area near the lower end of the range have been found effective, for example, for stopping bleeding and for treating certain respiratory conditions. For musculo-skeletal conditions, excellent results have been obtained in the range of 125-130 CFM/sq.in., and this is the most preferred range for treating such conditions.

Typical treatment distances between the outlet of the nozzle and the body may be of the order of 3-8 inches with 3½-6½ inches being the average, and typical treatment times are in the range of one to two hours with one and one-half hours being the average although treatment times as small as 10 minutes and as high as 16 hours may be used. In general, the greater the treatment time, the greater the penetration depth. A treatment time of one and one-half hours is sufficient to give a penetration depth of the order of two to three and one-half inches. Respiratory conditions have been treated successfully using treatment distances of the order of 15-18 inches from the nose or as close as 6 inches from the chest, treatment times of the order of 10-30 minutes, and outlet air temperatures of the order of 101°-102° F. To promote blood coagulation to stop bleeding of open cuts or wounds, treatment distances of 15-18 inches, temperatures of 101°-102° F., and treatment times of 1-10 minutes are preferred. Although positive results are typically seen following one treatment, if additional treatments are necessary, three to five days between treatments is preferred. This gives the body time to clear out defective cells which have been destroyed. Moreover, the effects of a single treatment have been observed to continue over a period of several days. For acute conditions, such as broken bones, treatments may, however, be given daily for several times to speed the healing process.

The following Examples detail actual treatments of individuals suffering from a variety of conditions, and illustrate the remarkable results afforded by the invention. Treatment parameters were in the previously given preferred ranges.

EXAMPLE I

Patient I, a 42 year old female, suffered a lower back injury and was admitted to the hospital where she was diagnosed as having a strained muscle that would require several weeks of hospital bed rest. After three weeks of bed rest with no therapy, her right leg swelled noticeably and became numb. Examinations revealed a swollen or protuded L-5 disc, with a posterior rupture of the annulus fibers of the intervertebral disc and with possible extrusion of the nucleus polposus into the subarachnoid space of L-5. Chiropractic care was non-productive, and the extruded parts were subsequently removed by surgery. Two months later the symptoms reappeared. The patient was told that the reason was the formation of scar tissue around the incision, and she was advised that she would have to live with the symptoms. She was listed as 30% permanently disabled.

At the time of treatment, the patient suffered numbness in the right leg and swelling from the hip to the foot, as well as pain in the lower back, especially during motion or prolonged sitting.

She was treated in accordance with the invention over the L-4, 5 and S-1 interspinous space and approximately two inches to either side of the spine. The treatment duration was two hours.

Following the treatment, there was a significant improvement in mobility of the lower back, decreased pain, and a feeling of exhilaration. The following day the pain had subsided, and good range of motion continued. She was retreated one week later in the L-5 area, which resulted in a complete arrest of her symptoms.

EXAMPLE II

Patient II, a 47 year old female, suffered degenerative disc disease of C-5 with brachial neuralgis to the left arm. At times, she suffered extreme pain in the neck, left shoulder, and left arm, which prevented sleep, and she exhibited a restricted range (50% decrease) of motion of the cervical spine.

She was treated in accordance with the invention in the C-5, 6 and 7 and in the left supra scapular regions. Treatment time was one and one-half hours. One treatment was sufficient to give complete relief of symptoms and no reoccurrences have been reported.

EXAMPLE III

Patient III, a 44 year old female, experienced chronic lumbo-sacral pain for a number of years, for which chiropractic treatments were ineffective. She experienced dull to sharp pains over the L-5 and S-1 area early in the morning and after sitting for short periods. X-rays revealed a very hyperlordotic lumbar curve with the articular facets of L-5 and S-1 being jammed together and weight-bearing. The facets displayed early hypertropic changes of arthritis.

She was treated in accordance with the invention for a period of about two hours. The treatment area was the facets of L-5 and S-1, which were treated from the posterior. Following treatment, the pain stopped and continued abated for a month. Approximately five weeks after the first treatment, she was again treated in the L-3, 4 and 5 area for a period of one hour and twenty minutes. There has been no return of symptoms.

EXAMPLE IV

Patient IV, a 42 year old male, suffered a lower back injury which resulted in rupturing of the L-5 disc. He underwent surgery for removal of the extruded parts, but within a few months his previous symptoms reappeared. He subsequently underwent additional surgery for removal of scar tissue trapping the L-5 nerve root. Six weeks after the second surgery, the symptoms again reappeared and became progressively worse. He experienced constant pain in L-5 area, and down the right leg into the foot. Occasionally there would be sharp shooting pains down the left leg also. The right leg became very weak and exhibited a notable decrease in calf size. X-rays confirmed a narrowed L-5 disc space with hypertropic degenerative changes present on the L-5 vertebral body margins as well as the sacral base. There was a total loss of toe strength in the right foot, with no feeling present from the ankle down. The right angle was also tender to the touch.

He was treated in accordance with the invention for approximately two hours in the L-4, 5 and S-1 areas from the posterior. Following the treatment, he began to have feeling in the toes of his right foot. His Achilles and popliteal regions were tender, and knee and ankle reflexes became equal in both legs. The pain in his right leg subsided, but there was a small muscle twitch in the leg for approximately 72 hours after treatment. Approximately a week later, he experienced minor pain in the left hip, right lumbar area, and distal to the right knee. He was given a second treatment in the same area for approximately two hours. After the second treatment, all pain subsided, Laseque tests were negative bilaterally, and he had a full range of motion.

EXAMPLE V

Patient V, a 49 year old male, suffered an acute intervertebral disc syndrome while working, and began to experience sharp lower back pains with pain and numbness in the left leg extending to the toes. He was unable to ambulate normally, and walked with an antalagic posture anteriorly and to the right. Arising from a sitting position was extremely difficult, as was sitting for more than a few minutes. X-rays revealed that the L-4 vertebral body was tilted dramatically to the right, causing welding of the L-4 and 5 discs. The lumbar spine was bent sharply to the right and kyphotic. The entire lumbar musculature experienced spasms and was tender to the touch. There was extreme pain produced to digital pressure over the L-4 and 5 interspace. Pain was traceable over the sciatic nerve to the heal of the left foot.

The patient was treated in the L-4 and 5 disc space from the posterior, with the patient in a side posture position. Treatment duration was approximately two hours. Immediately after treatment, the patient was able to get up and walk with little discomfort, and was able to bend over and touch his toes. There has been no reoccurrence of symptoms.

EXAMPLE VI

Patient VI, a 45 year old female, suffered from chronic recurrent lumbar pains caused by a left lumbar scoliosis. Chiropractic care had provided only temporary relief. She experienced continuous pain in her lower back, which interfered with sleep. X-rays revealed a mild left lumbo-dorsal scoliosis with the sacrum being tilted 4° high on the right. Her lumbar lordosis was reversed and there were asymmetrical facets between L-5 and S-1. The sciatic nerve was tender to her left foot, and her range of motion was normal.

She was treated for approximately an hour and one-half in the area of L-3, 4, 5 and S-1 joints. Following treatment, all pain was gone. She experienced some edema in her left thigh during the first night following treatment. The next day, the back pain was gone but the leg pain began to return slowly. She was given two additional treatments in the area between the sacral notch and the head of the femur. The pain abated after each treatment, but returned within approximately four weeks, although it was minor compared to the original pain and manifested itself as an intermittent soreness.

EXAMPLE VII

Patient VII, a 43 year old female, suffered from chronic lower back and hip pains due to a degenerative L-5 disc. X-rays of the lower back revealed a narrowed L-5 disc space with osteophytosis and eburnation present on the L-5 and sacral base. There was also an area of asthesia on the right posterior thigh centrally located.

She was treated in accordance with the invention for approximately two hours in an area centered over L-5. Following the treatment, the L-5 area was completely numb, and stiffness and pain had abated. A moderate amount of pain returned to the lumbo-sacral area, and a second treatment was given approximately six weeks later, which has provided complete relief from symptoms.

EXAMPLE VIII

Patient VIII, a 60 year old female, experienced severe arthritic pains in both knees. She was unable to bend her right knee fully, and sitting for a few minutes, or walking or standing for any extended period became extremely difficult due to pain. Walking over fifteen minutes caused her knee to swell and become stiff. She experienced pain in the right knee joint, with attendant endema from about two inches above and below the patella. X-rays of the right knee revealed that the joint space compromised on the medial half with a moderate increase in density of the femoral, tibial and fibular articular surfaces. The anterior inferior patella ligament showed a calcific density arising from the superior portion of the anterior tibial tuberosity.

The right knee joint space and surrounding area was treated in accordance with the invention for approximately two hours. The air was aimed into a ninety degree flexed knee, anterior to posterior. Immediately following treatment, the knee had complete freedom of movement, the pain was gone, and the swelling began to decrease. Three weeks after treatment, X-rays showed that the calcific spur was fifty per cent dissolved. Later X-rays showed it to be seventy-five per cent dissipated. She has continued to have complete use of the knee with no pain whatsoever.

Approximately a week following the first treatment, her left knee was treated for stiffness, joint noise, pain and swelling. Treatment duration was approximately two hours, with the air aimed from anterior to posterior through the ninety degree flexed knee joint. Following treatment, there was a decrease in endema and freedom from pain. There has been no reoccurrence of the symptoms.

EXAMPLE IX

Patient IX, a 43 year old female, began suffering from right brachial neuritis which prevented her from raising her arm and interferred with sleep. The condition progressed from mild neck pain to full blown neuralgias within a short period of time. X-rays revealed a reversed cervical curve with C-4 at the apex. Pain was traceable to the C-5, 6 and 7 nerve roots extending into the right arm and hand. Her neck was semi-rigid due to chronic paraspinal muscle spasms. The trapezius was spastic bilaterally and the right levator scapulae attachment to the scapula seemed to be a trigger point for pain. The grip strength in her right hand was reduced approximately eighty per cent.

She was treated in accordance with the invention in the C-4, 5, 6 and 7 areas from the posterior aimed superior to the inferior at a 45° angle. Treatment duration was one and a half hours. The right upper scapular was also treated.

Immediately following treatment, all pain and stiffness was gone, and the right shoulder exhibited a normal range of motion. Approximately a week later, some pain returned to the cervical spine and right elbow, which was relieved by manipulations of the cervical region. There has been no reoccurrence of symptoms.

EXAMPLE X

Patient X, a 42 year old female, suffered from a generalized neuralgias affecting many parts of her body, especially the limbs. She experienced burning-type pains after any physical exertion. She had been told that she had a liver problem which interfered with production of the proper protein coverings for the peripheral nerves.

She was treated in the area of the liver from the right side for a duration of approximately two hours. Within a week after treatment, all pain had abated and there has been no return of symptoms.

EXAMPLE XI

Patient XI, a 27 year old male, had been involved in a motorcycle accident which crushed his first and second lumbar vertebral bodies, leaving an acute kyphosis in the area. He underwent approximately five years of physical and rehabilitation therapy and was considered a paraplegic, requiring the use of a wheelchair and/or crutches with a thigh length leg brace on the left leg and knee length brace on the right leg. He experienced pain in the upper lumbar area daily, and had pains in his calf below his left knee and in both knee joints. These pains appeared to be of an arthritic nature. X-rays revealed a crushed L-1 vertebral body, juxtapositioned posteriorly to T-12 and L-2. There was fusion of T-12, L-1 and L-2 by osteophytosis of the bodies, and the posterior facets were arthritic and appeared intact, though grossly posterior at L-1. The L-1 vertebral body was wedged anteriorly with total loss of disc height above and below it, causing an acute kyphosis of the lumbo-dorsal spine. Each leg was totally atrophied from the middle thigh. There was no muscle tone or reflexes in the knees or lower legs, and there was absence of feeling except for very slight deep pressure responses. The left knee had a large raised area over the medial phemeral condyle. X-rays of the left knee showed calcific infiltrations of most tendons in the area.

The patient was given several treatments in accordance with the invention. The first treatment, which lasted for approximately two and a quarter hours, covered the areas of T-12, L-1, L-2 and L-3 over and above two inches to each side of the spine. Toward the end of the treatment, he experienced a tingling in his feet and what he described as a sensation that his feet were beginning to swell. Shortly before the end of the treatment, he experienced a sharp pain in his posterior thighs and feet. Immediately after treatment, he experienced severe intestinal cramps and groin pains with nausea. These lasted for slightly more than an hour, at which point all pain subsided. Approximately four days after the treatment, he as able to pull his right lower leg backwards for the first time since his accident, and reported an occasional pain in his right thigh.

A second treatment was given one week following the first treatment in the area of T-12, L-1, 2 and 3. Treatment duration was two hours. After treatment, the patient was able to move his left lower leg backwards slightly, and was able to flex his right foot against slight resistance for the first time. He experienced no pain and felt very relaxed.

A third treatment was given approximately one week later in the same area. The duration was one and one-half hours. Approximately one-half hour into the treatment, he described a strong tingling sensation from his back to his feet, which lasted throughout the rest of the treatment. He again suffered intestinal cramps immediately afterwards, but they were mild and lasted for only a short period of time. There had been tenderness in the soles of his feet before the treatment, which was relieved. He was able to feel light touch in his entire right leg, and reported that his right leg could now pull up twenty-five pounds in lower leg extension using home exercise equipment. Approximately two weeks later he reported that he was able to lock and balance on his right leg without a brace, which had previously been impossible. The left knee could still not be locked while standing erect and support him. His right foot, however, was becoming stronger in plantar flexion.

He was given a fourth treatment in the left knee area approximately three weeks following the third treatment. Treatment duration was one and one-half hours. The air was aimed at the flexed knee joint from a medial to lateral angle of approximately sixty degrees to ensure treating the femoral area. There were occasional sharp pain sensations into the calf area and the foot during the last half of the treatment, and the bottom of his foot experienced noticeable tingling sensations throughout the treatment. Immediately after the treatment, he was able to stand and lock the left knee. There was considerable joint noise on movement, especially in the sub patellar region.

As a result of the treatments, the patient regained much of the use of his right leg, and is now able to stand on the right leg with a brace. The brace extends only to just inferior of the knee and is principally for ankle stabilization. The right calf muscles have exhibited a dramatic improvement in size and strength. The left leg, although still weak, exhibited slow improvement following the treatments. The sensations of light touch have returned to the right leg, but not to the left, and the patient is now able to walk using only one crutch in the left hand and a brace. There has been no return of any of the pain.

EXAMPLE XII

This patient suffered from chronic rheumatoid arthritis for a period of twenty-seven years resulting in her hands being curled, partly disjointed, and badly deformed with hugh protruding nodules and chronic pain which significantly interfered with the use of her hands. She also had nodules on her feet which made walking or standing difficult.

She received a total of six treatments of one and one-half hours each, three treatments on both hands together, two on her right foot, and one on her left foot. After each treatment, noticeable receeding of the old chronic nodules was evident, and there was a significant reduction in pain. After the six treatments, most of the nodules disappeared and she regained almost complete flexibility of her hands and the ability to walk or stand without pain in her feet.

EXAMPLE XIII

This patient also suffered from rheumatoid arthritis for many years, and had chronic nodules and overgrown joints on both hands with associated chronic pain.

She had a total of five treatments. After the second treatment, the pain was gone in both hands, circulation was improved, and a noticeable reduction in the size of the nodules occurred. Continued treatments afforded still further improvement, and there has been no return of symptoms.

An interesting sidelight occurred during the treatments. The patient had a large scar which was many years old on the palm of one hand under the index finger. The scar protruded outwardly approximately ⅛ inch, and through the years had remained tender. After the third treatment, the scar and the associated tenderness had almost completely disappeared.

EXAMPLE XIV

The patient was a fourteen year old girl who, as a result of surgery, had a large ugly scar on the distal part of her left femur just above the knee. The scar was about a year old, was purple in color, and one end protruded outwardly noticeably. She was unable to walk for any sustained period without pain due to adhesions in the muscle surrounding the scar, which caused her to limp after routine movements and prevented her from participating in sports.

She received a total of four treatments on the scar. After the third treatment, the scar had turned brown, the protruding portion which previously had been a hard knot turned soft, and the pain was eliminated. As a result of the treatments, the scar tissue on the surface of the leg and adhesions under the surface which were causing the pain were substantially dissolved, enabling her to engage in strenuous exercise without pain. There has been no reoccurrence of symptoms.

EXAMPLE XV

The invention was employed for the treatment of seven different cases of acute sprains resulting from sports injuries. The sprains included five ankle sprains, one elbow sprain and one finger sprain. The ankle sprains varied from chronic recurrent to acute moderate, and were treated within hours of the injury and again on the following day. Treatment times varied between 45 minutes and one and one-half hours. In general, a significant decrease in pain was noted after the first treatment, and following the second treatment all edema and pain had been eliminated, enabling the patients to return to sports within two days following the original injury. The elbow and finger sprains were healed after one treatment.

The foregoing Examples are merely illustrative of a few of the various types of conditions which may be treated in accordance with the invention, and they demonstrate vividly the remarkable results obtainable using the invention. For many of the patients described in the foregoing Examples, conventional surgical, medical or chiropractic treatment methods had been ineffective or only partially effective. In contrast, treatment methods in accordance with the invention, which are non-invasive and require only rather simple apparatus, have been remarkably effective in treating conditions such as these, as well as other conditions in a living body produced by injury or by defective cells.

While a preferred embodiment of the invention has been shown and described, it will be appreciated by those skilled in the art that changes may be made in this embodiment without departing from the principles and spirit of the invention, the scope of which is defined in the appended claims.

What is claimed is:

1. A method of treating a condition in a living body comprising applying to an area of the body in which said condition is located infrared electromagnetic energy having a wavelength such that the energy is absorbed by body cells in said area, the energy being derived from a flowing gas that is applied externally to the body adjacent to said area, adjusting the temperature of the gas applied to the body to a value of approximately 108° F. or less so as to produce at said area an internal temperature within the normal temperature operating range of the body, the wavelength of the energy being determined by said internal temperature, and adjusting the amplitude of the energy, by adjusting the flow rate of the gas, to a value that is effective to treat said condition.

2. The method of claim 1, wherein said condition is produced by defective cells, and the amplitude of the energy is adjusted to a value that is effective to destroy the defective cells without substantially destroying healthy cells.

3. The method of claim 1 further comprising employing said energy for energizing healthy cells in said area.

4. The method of claim 1, wherein the energy is selected to have a wavelength so as to produce a cellular-type resonance.

5. The method of claim 4, wherein the wavelength is in the nine to ten micron range and said normal operating temperature range is of the order of 96°–104° F.

6. The method of claim 5, wherein said internal temperature has a median value of the order of 102°–104° F.

7. The method of claim 1, wherein said condition is a musculo-skeletal condition.

8. The method of claim 1, wherein said condition comprises scar tissue accumulation and said treating comprises dissolving the scar tissue.

9. The method of claim 1, wherein said condition is one produced by injury.

10. The method of claim 1, wherein said condition is a respiratory condition.

11. The method of claim 1, wherein said gas is air, and said applying comprises directing heated air onto the body substantially perpendicular thereto at an external location adjacent to said area.

12. The method of claim 11, wherein said air has a temperature greater than the desired internal temperature by an amount at least equal to a skin-to-internal temperature differential of the body.

13. A method of treating a condition in a living body by using apparatus for applying to the body infrared electromagnetic energy having a wavelength such that the energy is absorbed by body cells and having an amplitude that is effective to treat said condition, the energy being derived from a gas flow that is applied to an external location of a body adjacent to an area containing the condition, the apparatus comprising means for producing a gas flow; means for directing the gas flow to a desired location; heater means for heating the gas flow; temperature measuring means for measuring the temperature of said gas flow; and means responsive to the temperature measuring means for controlling the heater means so as to maintain a desired temperature of the gas flow, said method comprising directing, using said directing means, the gas flow to said external location of the body, and maintaining, using said controlling means, the temperature of the gas flow applied to the external location of the body at approximately 108° F. or less and so as to produce a predetermined internal temperature in said area containing the condition, the predetermined internal temperature being related to said gas flow temperature.

14. The method of claim 13, wherein said condition is produced by defective cells, and the method comprises adjusting the amplitude of the energy to a value that is effective to destroy the defective cells without substantially destroying healthy cells by controlling said producing means to afford a predetermined gas flow rate.

15. The method of claim 13, wherein said maintaining comprises maintaining the gas temperature such that the predetermined internal body temperature is in the range of 96° F. to 104° F. the internal temperature defining the wavelength of the energy.

16. The method of claim 15, wherein said maintaining comprises maintaining the internal body temperature to have a median value in the range of 102°–104° F.

17. The method of claim 13, wherein the amplitude of said energy is related to the flow rate of said gas, and wherein the apparatus includes means for controlling the gas flow rate, and said method comprises controlling the gas flow rate controlling means so as to produce a predetermined gas flow rate.

18. The method of claim 17, wherein said controlling comprises controlling the gas flow to have a value in the range of 46 CFM/sq.in. to 150 CFM/sq.in.

19. The method of claim 18, wherein said controlling comprises controlling the gas flow to be in the range of 125 CFM/sq.in. to 130 CFM/sq.in.

20. The method of claim 17, wherein said gas flow producing means comprises a blower driven by a motor, said directing means comprises a nozzle positioned on an outlet of the blower, and the gas flow rate and gas temperature are measured at the outlet of the nozzle, and wherein said maintaining comprises maintaining the gas temperature at the nozzle outlet at a predetermined value, and said controlling comprises controlling said motor.

21. The method of claim 20, wherein said heater means is disposed at an inlet of said blower for heating the inlet gas thereto, and wherein said maintaining comprises controlling the heater means controlling means so as to provide a gas temperature in the range of 98° F. to 108° F.

22. The method of claim 21, wherein said heater means comprises heating coils disposed within a member positioned at the inlet of the blower, and means for supplying to said member heat produced by the motor, and wherein said maintaining comprises controlling electrical current to said coils.

23. The method of claim 22, wherein said supplying means comprises a duct connected to the motor and having an opposite end positioned about a tubular inlet of the member that has a smaller size than the duct, and wherein said maintaining comprises drawing heat from the motor through the duct.

24. The method of claim 13, wherein said applying comprises applying said energy for a predetermined period of time.

* * * * *